US005640488A

United States Patent [19]

Junqua et al.

[11] Patent Number: 5,640,488
[45] Date of Patent: Jun. 17, 1997

[54] SYSTEM AND METHOD FOR CONSTRUCTING CLUSTERED DICTIONARY FOR SPEECH AND TEXT RECOGNITION

[75] Inventors: Jean-claude Junqua, Santa Barbara; Craig Demel, Goleta, both of Calif.

[73] Assignee: Panasonic Technologies, Inc., Princeton, N.J.

[21] Appl. No.: 435,882

[22] Filed: May 5, 1995

[51] Int. Cl.⁶ .................................................. G10L 5/00
[52] U.S. Cl. .................. 395/2.54; 395/2.52; 395/2.53; 395/2.6; 395/2.61
[58] Field of Search .......................... 395/2.4, 2.43, 395/2.47–9, 2.5, 2.52–4, 2.6, 2.61

[56] References Cited

U.S. PATENT DOCUMENTS 4,975,959  12/1990  Benbassat .................. 381/41

OTHER PUBLICATIONS

Wilpon, J. And Rabiner, L., "A Modified K–Means Clustering Algorithm for Use in Isolated Work Recognition,"
*IEEE Transactions on Acoustics, Speech and Signal Processing*, vol. ASSP–33, No. 3, Jun. 1985, pp. 587–594.

*Primary Examiner*—Allen R. MacDonald
*Assistant Examiner*—Robert Sax
*Attorney, Agent, or Firm*—Harness, Dickey & Pierce

[57] ABSTRACT

The dictionary is broken into clusters by first grouping the dictionary according to a rule based procedure whereby the dictionary is sorted by word length and alphabetically. After sorting, a plurality of first cluster centers is generated by selecting the dictionary entries that differ from neighboring entries by the first letter. Each of the dictionary entries is then assigned to the closest one of the first cluster centers using a dynamic time warping procedure. These newly formed clusters are then each analyzed to find the true cluster center and the dictionary entries are then each assigned to the closest true cluster center. The clusters, so formed, may then be rapidly searched to locate any dictionary entry. The search is quite efficient because only the closest cluster to the desired dictionary entry needs to be searched.

7 Claims, 10 Drawing Sheets

FIGURE 4

[Excerpt from First Clusters]

--- cluster Center 1 (ab) identifies 5 words

--- ab
ag
al
an
au

--- cluster Center 2 (by) identifies 1 word

--- by

---
---

∙
∙
∙

---
--- cluster center 273 (schellenberger) identifies 2 words

--- schellenberger
stewartguthrie

| | | | |
|---|---|---|---|
| ab is the center of cluster 1 | ku | abbatantuono | papadopulos |
| | la | adaline | papageorges |
| | le | adminmtv | papajanis |
| | li | aidarous | papantonis |
| | lu | akkermans | pashmineh |
| | ly | aldhizer | relations |
| ab | mab | amavisca | rodriques |
| abe | mc | ansorger | saravanos |
| ag | mo | aramideh | services |
| al | nat | aribindi | zacharias |
| an | ned | associates | |
| au | ng | athanassiadis | |
| aub | op | benavides | • |
| bab | qu | bookings | • |
| bo | rab | braginetz | • |
| co | rad | casadonte | |
| cy | red | costadimas | |
| da | rk | cuddihey | |
| db | saba | cummings | winje is the center of cluster 273 |
| de | sabo | dauphinais | |
| deb | si | deguines | |
| di | st | dermardiros | |
| eby | st | desharnais | aimee |
| ed | su | dikaitis | cinda |
| em | sy | dulcinea | circe |
| eo | ta | estabrooks | ince |
| er | tab | eteminan | kimma |
| eu | td | godcharles | linda |
| ev | ty | hammonds | linde |
| ez | us | handrinos | lindt |
| fab | vi | hastings | linea |
| fu | vo | hitchings | linet |
| gu | vu | hoddinott | linke |
| hr | wu | hutchings | minda |
| hu | xu | hyacinth | sinha |
| hy | yu | hyacintha | sonja |
| ic | zeb | hyacinthe | vince |
| id | zed | joannidis | vinet |
| ip | | johannes | wiebe |
| iu | | klaudinyi | wiese |
| jeb | abadines is the center of cluster 2 | koskinen | wigle |
| jed | | measures | winje |
| jo | | mohammed | winna |
| ki | | muhammed | winne |
| ko | abadines | obadias | wynne |

SYSTEM AND METHOD FOR CONSTRUCTING CLUSTERED DICTIONARY FOR SPEECH AND TEXT RECOGNITION

BACKGROUND AND SUMMARY OF THE INVENTION

The present invention relates generally to speech and text recognition. More particularly, the invention relates to a system and method for constructing a computer-searchable dictionary. The system organizes the dictionary into clusters to facilitate rapid dictionary searches. The system constructs a clustered dictionary through a process that is much faster than conventional dictionary ordering processes. This enables much larger dictionaries to be clustered while minimizing processor overhead.

Speech recognition systems and text recognition systems often rely on comparing the input test speech or input text with entries in a dictionary. The dictionary is a database containing all possible entries that the recognition system is capable of processing. In a simple text-based system it is possible to organize the dictionary alphabetically, using a tree-structured data structure to store the dictionary. The alphabetically-sorted, tree-structured dictionary works well when the confusability between speech fragment utterances or text characters is low. However, the alphabetically-sorted, tree-structured dictionary does not work well when there is a moderately high likelihood of confusion among utterances or letters.

To demonstrate, in a keyboard entry text application, the identity of each keystroke can be treated as reliable. Thus, as a word is typed, the dictionary searching algorithm can traverse the alphabetically-sorted tree, letter by letter, thereby progressing to the dictionary entry as it is typed. In a speech recognition system, or in any text input system in which the individual speech fragment utterances or letters cannot be deemed reliable, the alphabetically-sorted, tree-structured dictionary gives poor results. For example, if the first input speech fragment utterance or character is confused or misinterpreted, an alphabetically-sorted, tree-structured algorithm will begin to traverse an incorrect path. Thus, if the letter J is mistaken for the letter G, the tree-structured algorithm will fail to find the entry JOHNSON, by having misconstrued the first letter.

Accordingly, in speech recognition and text recognition systems with moderately high probability of confusion, a clustered data structure is preferred. To build a conventional clustered data structure, the dictionary of all possible entries is mapped onto an N×N distance matrix (N being the number of entries in the dictionary) in which the distance of each entry from all other entries is calculated and recorded in the matrix. Distance can be computed using a variety of different metrics, the simplest being the geometric distance calculated using the Pythagorean theorem upon the individual parameters that are used to define the dictionary entries. For example, if each dictionary entry is represented by 3 parameters, a, b and c, the distance between two entries is computed according to the Pythagorean theorem as follows.

$$d = \sqrt{(a_2 - a_1)^2 + (b_2 - b_1)^2 + (c_2 - c_1)^2}$$

The conventional clustered data structure is constructed by examining the n×n distance matrix to find the center of the dictionary; then find the point where the distance from all other points is maximum; and then reassign all points to these two cluster centers. The cluster centers are then computed again and the process is repeated iteratively until the desired number of clusters is generated.

Specifically, these two points are used to divide the dictionary into two subsets corresponding to the two points identified. Each entry in the dictionary is assigned to one subset or the other, depending on which of the two points the entry is closest to. The procedure is then repeated again and again, until the original dictionary has been broken into the desired number of subsets or clusters.

The conventional technique for generating these clusters is suitable for small dictionaries, such as on the order of several thousand entries. However, as the dictionary size increases, the conventional cluster forming technique becomes geometrically slower to construct and use rapidly too much memory. Whereas a small dictionary might be subdivided into a suitable number of clusters in a manner of minutes, a large dictionary could take days, weeks or even years to construct in this conventional fashion. The time required to construct the dictionary clusters can pose significant penalties on systems that are designed to periodically merge data from separate dictionaries into a single dictionary, as this may frequently necessitate recomputing the cluster centers.

The present invention takes a different approach to constructing a clustered dictionary. According to the invention, the initial dictionary is first subdivided according to a predefined rule-based system to provide a plurality of first cluster centers. By way of example, the rule-based system may sort the dictionary alphabetically and then divide the dictionary into groups based on the number of letters contained in each word entry. Within each length category all words that differ by the first letter are used as a first cluster center. The cluster centers identify the words or names of the same length that begin by the same letter. That is the presently preferred rule-based system for providing the first cluster centers. In general, however, any suitable rule-based system that produces the desired number of cluster centers may be employed. The number of cluster centers generated by the rule-based system is dictated largely by processor speed and desired time constraints. The presently preferred system selects on the order of 260 cluster centers for a 20,000 word dictionary.

Having selected the first cluster centers, all entries in the initial dictionary are compared to each of the cluster centers. At least a portion of the dictionary entries are assigned to the closest cluster center, thereby subdividing the initial dictionary into a plurality of first clusters.

Next, each of the first clusters is examined to identify its true cluster center, thereby defining a plurality of second cluster centers. The first cluster centers and the second cluster centers do not necessarily match one another even though they may be associated with the same one of the first clusters.

Having identified the second cluster centers, the initial dictionary is subdivided into a plurality of third clusters by comparing each entry of the initial dictionary to each of the second cluster centers, and assigning each entry to the one of the second cluster centers that represents the closest degree of similarity.

The above process of identifying the cluster centers and reassigning each entry of the initial dictionary to the closest center may be repeated over a series of iterations, if desired. The system provides a clustered dictionary for electronic speech and text recognition applications, without the costly computational overhead found in conventional cluster generation systems. For a more complete understanding of the invention, its objects and advantages, refer to the following specification and to the accompanying drawings.

BRIEF DESCRIPTION OF THE DRAWINGS

FIG. 4 is a schematic for depicting how to develop the Level 1 centers;

FIG. 10 is an example of the second clusters.

DETAILED DESCRIPTION OF THE PREFERRED EMBODIMENTS

Figure 1:
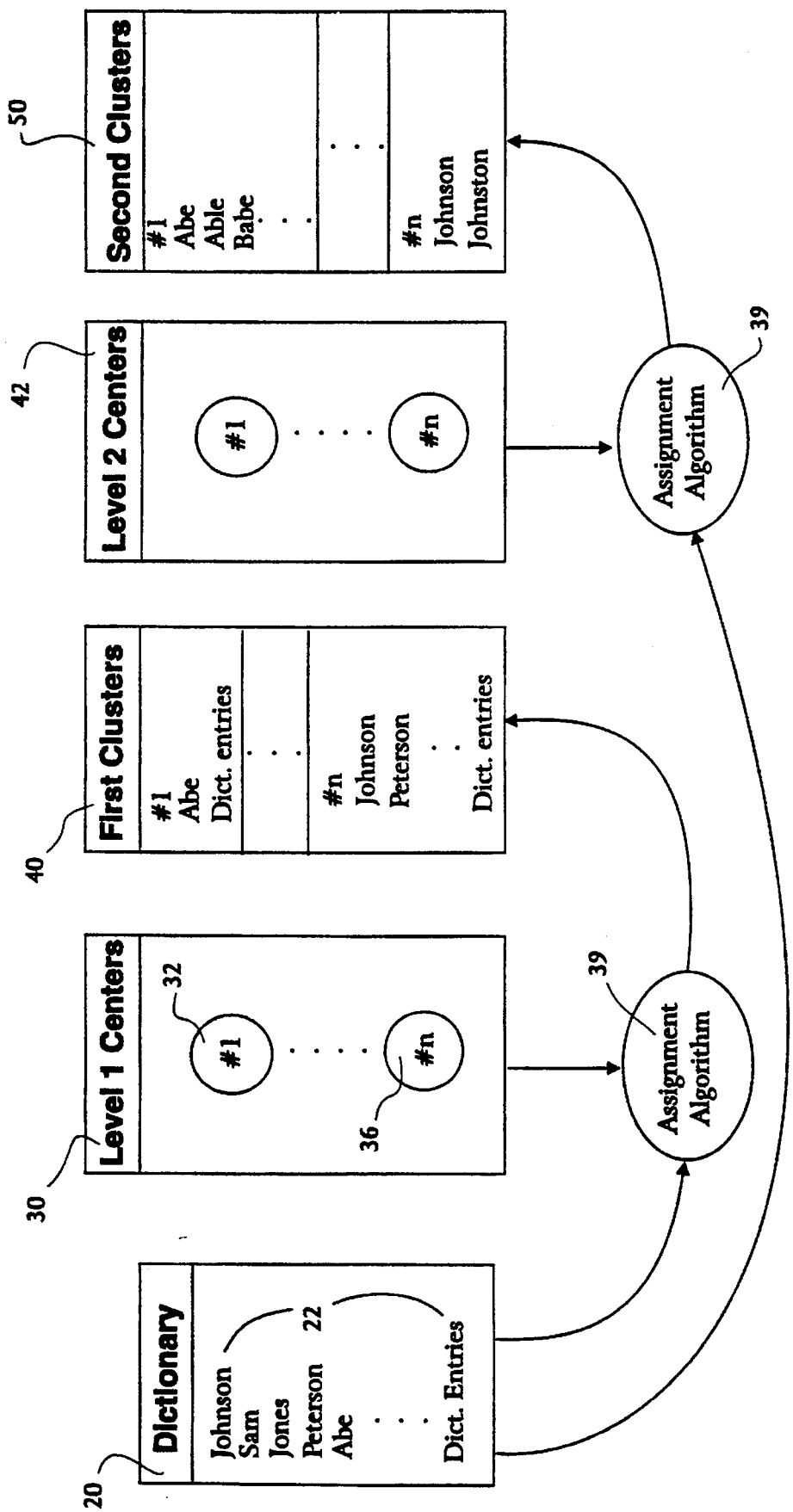
FIG. 1 is a flow diagram that shows the various levels of the database clustering system.

The overall database clustering system is depicted in the flow diagram of FIG. 1. A dictionary 20 is provided as input into the database clustering system. The dictionary 20 is comprised of dictionary entries 22. In the illustrated example these dictionary entries 22 are words that will be used eventually as input into a word recognition system. The number of entries in a dictionary may range from only several entries to several tens-of-thousands of entries. While small dictionaries may be quickly searched to locate words needed for word recognition, large dictionaries pose problems of slow access time that can debilitate a word recognition system. The present invention addresses the problem of how to quickly search large dictionaries by a new technique for clustering the dictionary.

Overview

Before presenting a detailed description, a brief overview will be given while referring to FIG. 1. In FIG. 1, the dictionary 20 is broken up into a set of cluster centers. This initial set of cluster centers is called the "Level 1 centers" 30.

Any rule-based technique may be used to break up the dictionary into the Level 1 centers. The presently preferred embodiment sorts the dictionary alphabetically and by word length, using the first word of each different word length as a cluster center. The Level 1 centers 30 comprise cluster centers #1 to #n (designated by reference numerals 32 and 36) where n is any integer number of the desired number of clusters.

The dictionary entries 22 are compared to each of the Level 1 centers by an assignment algorithm 39. The assignment algorithm 39 assigns each dictionary entry to the closest cluster center. The assignment of each entry of the entire dictionary to one of the Level 1 cluster centers by the assignment algorithm 39 produces the first clusters 40.

Next, the center of each of these first clusters is found to yield Level 2 centers 42 and compared to each dictionary entry by the assignment algorithm 39 to form the second clusters 50. These second clusters represent a novel and efficient break up of the dictionary 20 for more quickly searching the dictionary 20. If desired further iterations can be performed according to this strategy.

Figure 2:
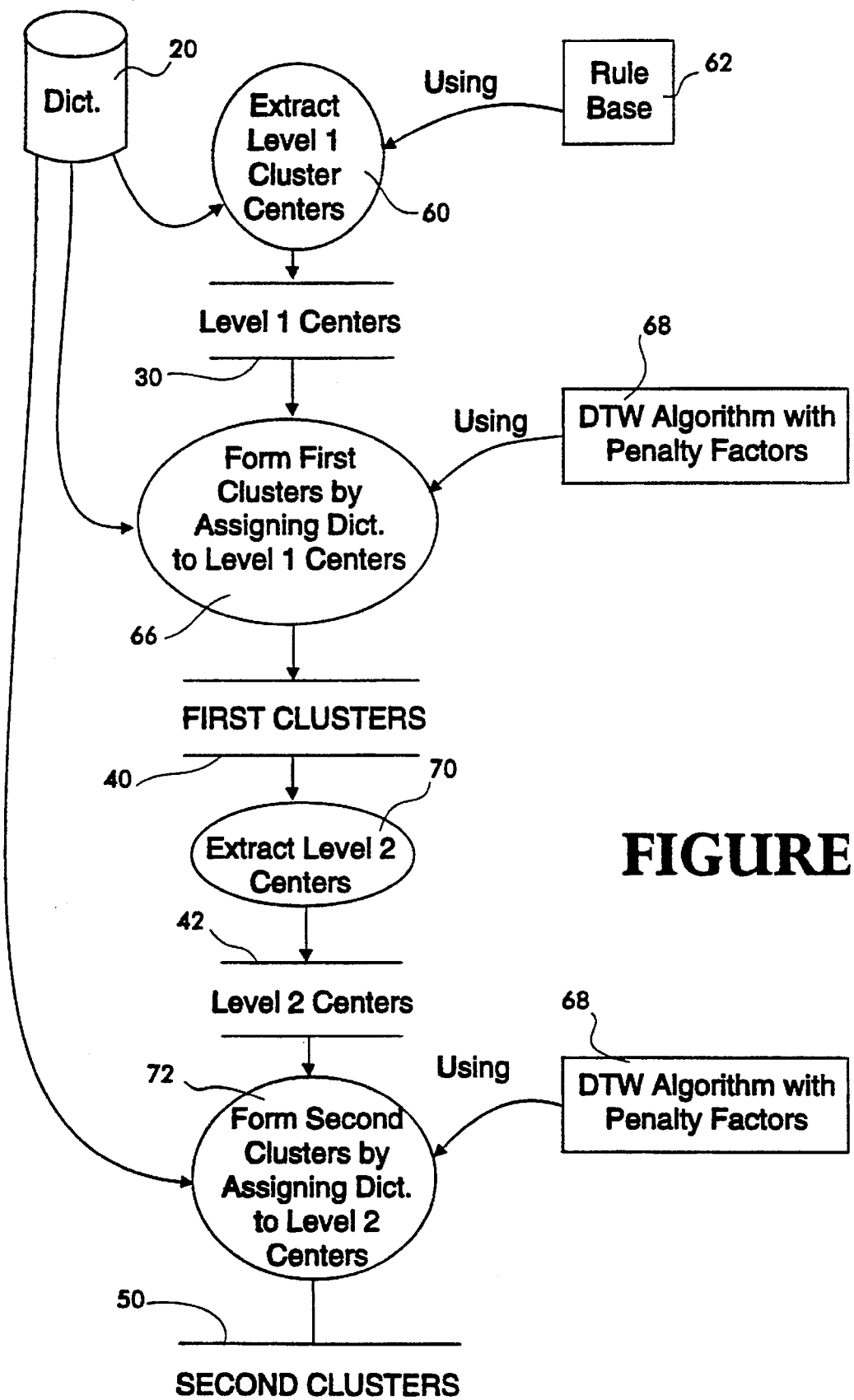
FIG. 2 is a flow diagram that shows the database clustering system procedural overview.

FIG. 2 shows the top-level steps to produce the various levels of cluster centers and clusters for a dictionary 20 as depicted in FIG. 1. The first step 60 is to extract from the dictionary 20 the Level 1 centers 30 based upon the Rule Base 62. The next step 66 is to form the first clusters 40 by assigning the dictionary entries to the Level 1 cluster centers. The distance of each dictionary entry 22 to a Level 1 center is computed by the DTW algorithm with applied penalty factors 68. The next step 70 is to develop Level 2 centers 42 for each of these newly formed clusters. The final step 72, is to form the second clusters 50 by reassigning the dictionary 20 to Level 2 centers. The distance from each dictionary entry 22 to a Level 2 cluster center is computed by the DTW algorithm 68.

Detailed Procedural Discussion

Figure 3:
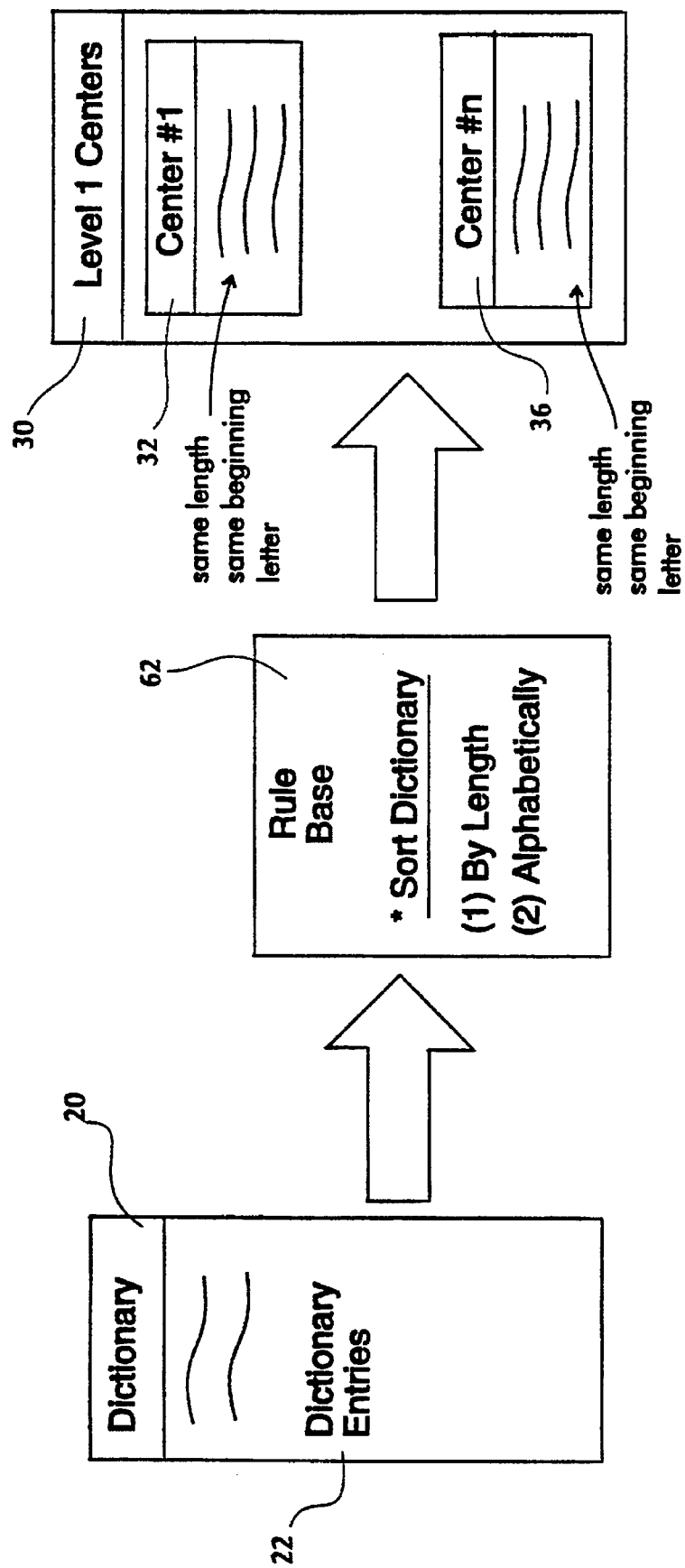
FIG. 3 is a flow diagram depicting the break up of the dictionary into the Level 1 centers.
Figure 5:
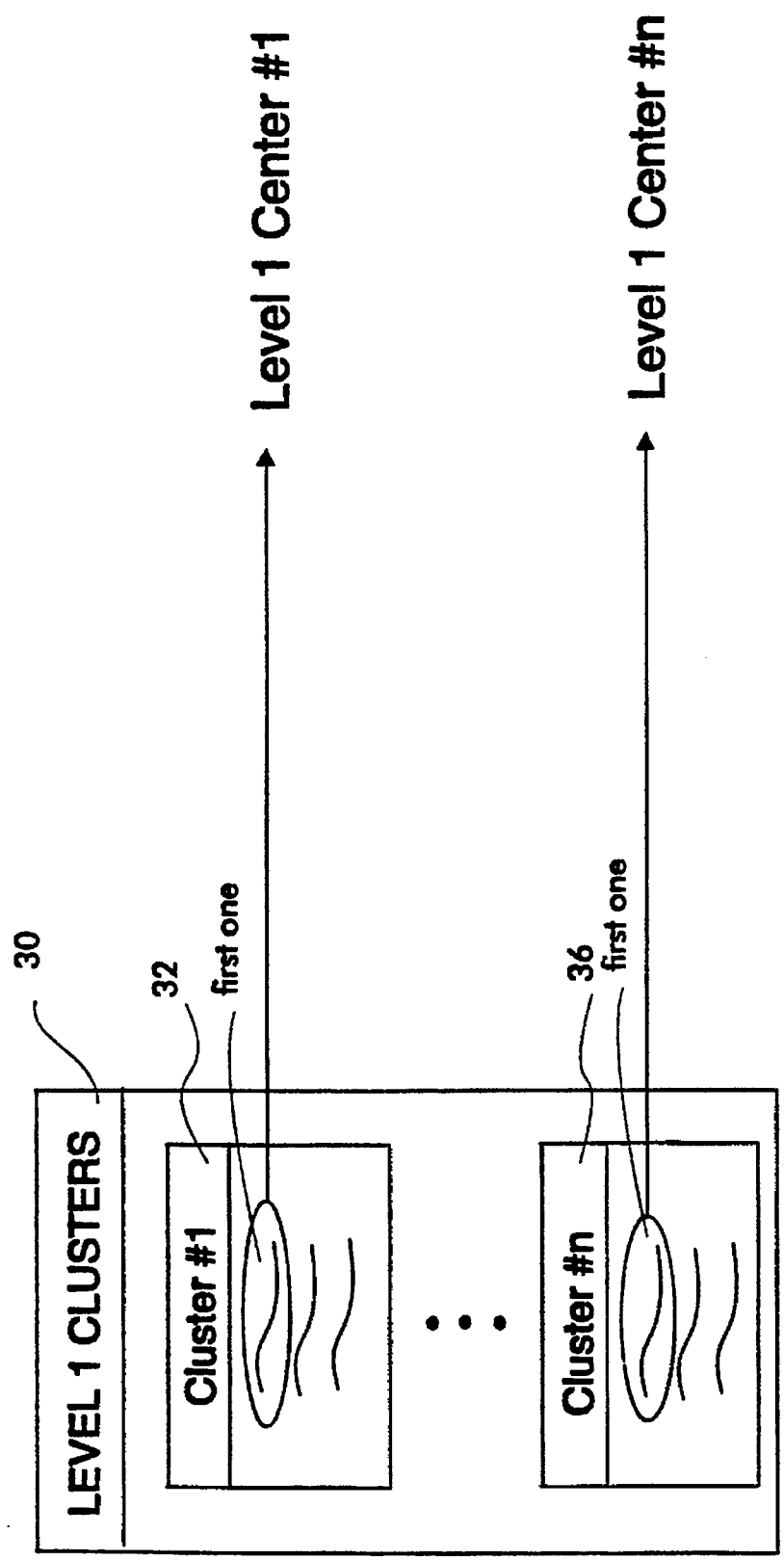
FIG. 5 is an example of Level 1 cluster centers.

As shown in FIG. 3, a Rule Base 62 is used to break up the dictionary 20 into the Level 1 centers 30. Although a variety of different rule based strategies may be used, the presently preferred Rule Base 62 provides that the dictionary 20 be sorted by the length of the dictionary entries. Then, the Rule Base 62 sorts the dictionary entries 22 alphabetically. These two rules arrange the dictionary 20 into a dictionary that starts with the smallest length words and progresses up to the largest length words; and within each group of words that have the same length, the words are sorted alphabetically. Each Level 1 center is determined by finding the words that differ by the first letter. FIG. 5 further depicts how the Level 1 centers are then determined. After the dictionary has been sorted by length and alphabetically according to the Rule Base 62, the first word that differs from its preceding neighbors by the first letter is selected as being that particular cluster's center. For instance, in the following sorted list, the word BAT would be chosen as a Level 1 center, because it differs from its preceding neighbor AZT by the first letter.

```
ABE
ATE
AZT
BAT    ← Level 1 Center
BOG
```

The number of centers in Level 1 will vary based upon the entries in the dictionary 20. Typically, the number of cluster centers in Level 1 range in the upper 200s. FIG. 4 is an example of clusters #1, #2 and #273 of Level 1.

Figure 6:
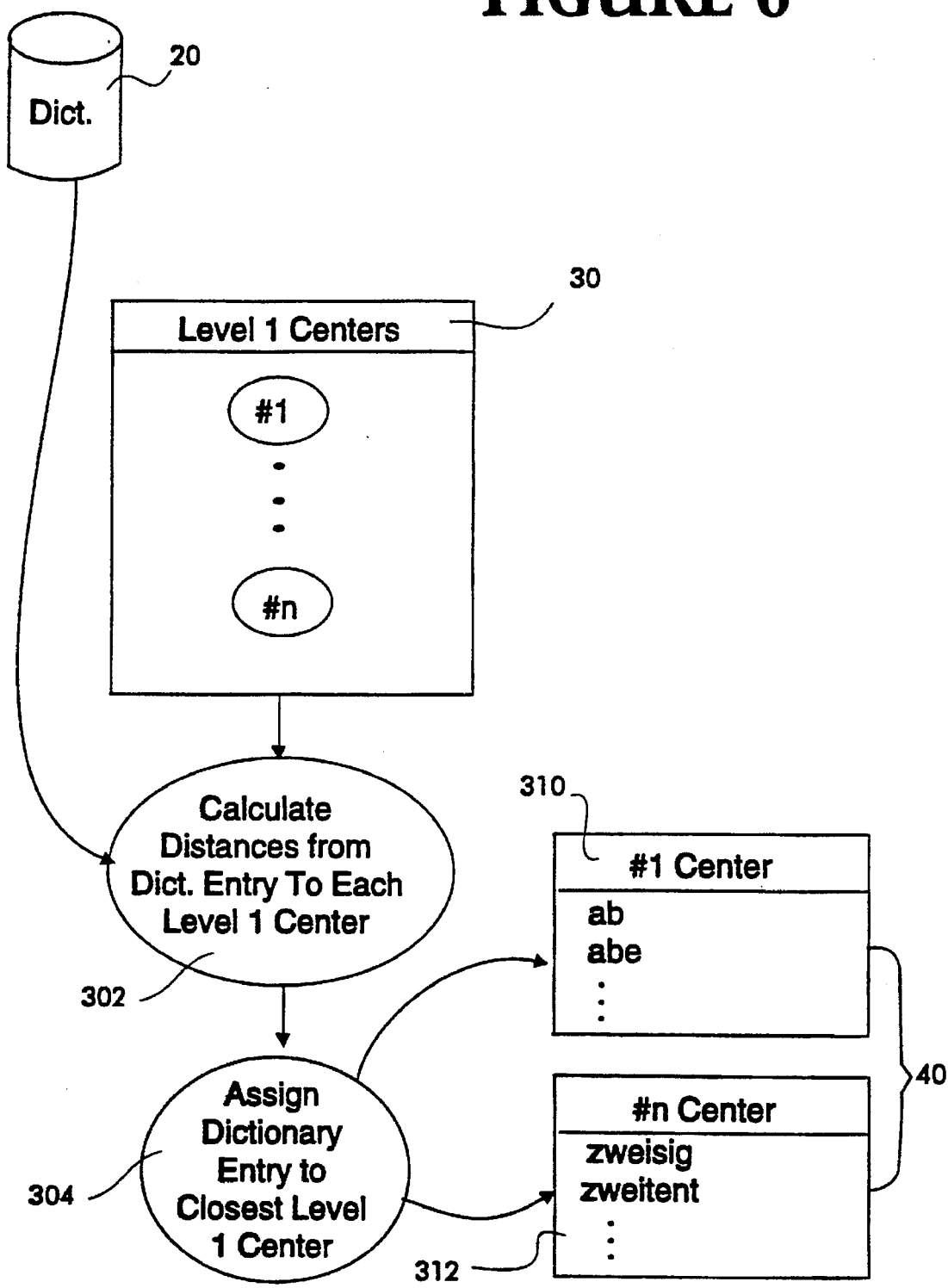
FIG. 6 is a flow diagram that shows the formation of first clusters by assigning the dictionary entries to the Level 1 cluster centers.

FIG. 6 illustrates how the first clusters are formed. The dictionary entries 22 are each compared to each of the Level 1 centers by a weighted distance algorithm. The preferred embodiment uses a dynamic time warping (DTW) algorithm. Each dictionary entry is then assigned to a cluster corresponding to the Level 1 center that is closest to that entry. After this has been done for the entire dictionary a plurality of first clusters will have been formed.

Figure 7:
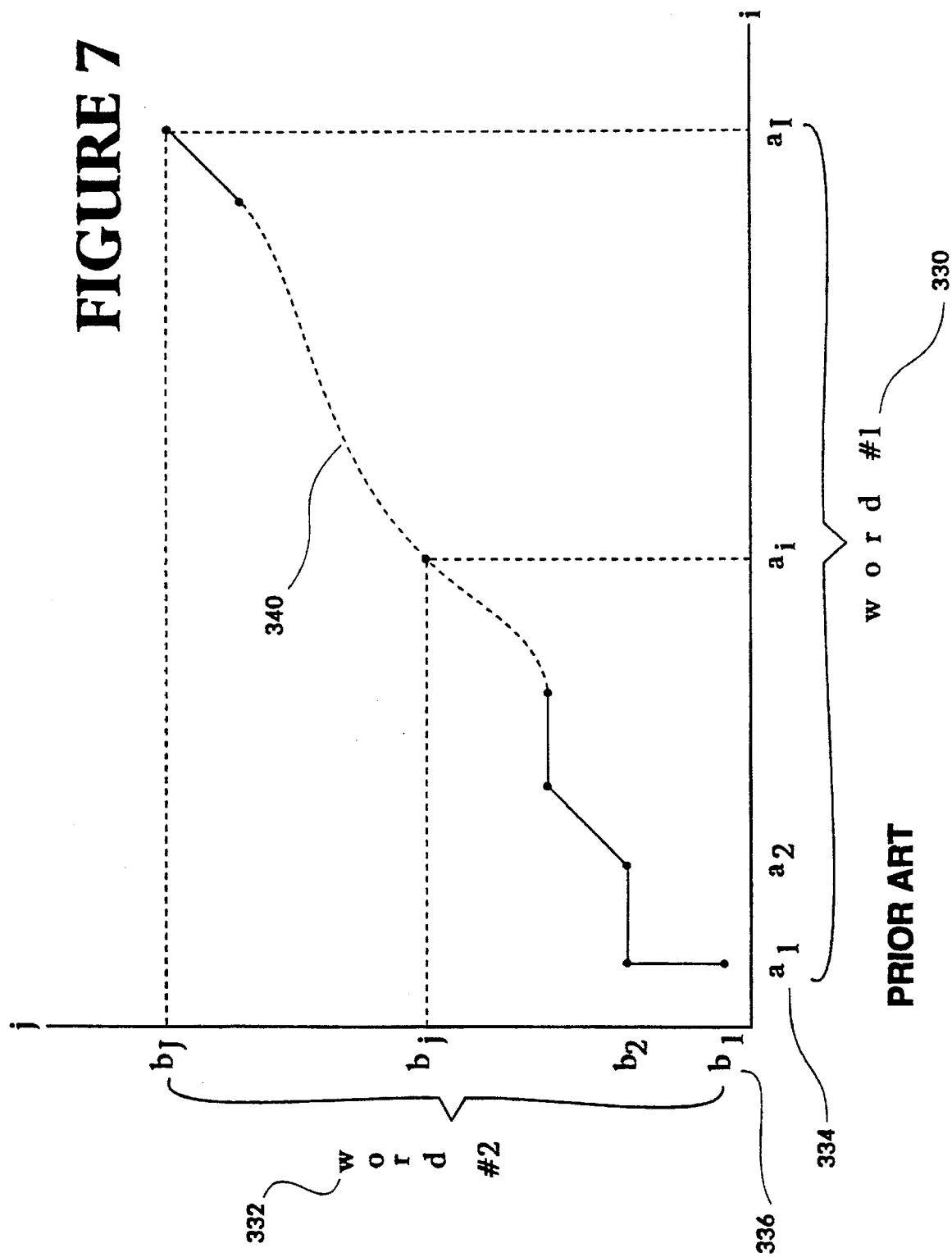
FIG. 7 is a graph depicting the comparison of two words by using the dynamic time warping (DTW) algorithm.

FIG. 7 illustrates the concepts employed by the DTW algorithm. FIG. 7 graphically shows how two words may be compared on the basis of the word's respective feature vectors. Word #1 330 is placed on the abscissa axis and a word #2 332 is placed on the ordinant axis. Each word is broken up into feature vectors (such as feature vectors, a, 334 and b, 336). In this case the feature vectors may simply represent the component letters that make up the word. The feature vectors of word #1 are compared against the feature vectors of word #2. The accumulated distance between the feature vectors of word #1 and #2 is calculated and represented by the curve 340. A summation of all these distances indicates how "good" is the match between word #1 and word #2. The smaller the summed distance, the better is the match between word #1 and word #2.

The DTW algorithm used here includes a penalty factor for calculating the distance. The distance values are penalized (i.e., increased) whenever a particular word's feature vector has been substituted, inserted or deleted. Furui, on pages 244–247 of *Digital Speech Processing, Synthesis, and Recognition*, provides a more detailed examination of the DTW algorithm.

A return to FIG. 6 shows in step 302 how the DTW algorithm is used to form the first clusters. (The same algorithm may be used to form the second clusters that will be discussed below.) The DTW algorithm takes as word #1 a particular dictionary entry. Then, it takes as word #2 a Level 1 center. A distance value is obtained that represents how well the dictionary entry matches a particular Level 1 center. Then, at Step 304, the dictionary entry is assigned to a first cluster 40 that represents the closest match. Clusters 310 and 312 depict those dictionary entries that were closest to the Level 1 center to be assigned to centers #1 and #n, respectively.

Figure 8:
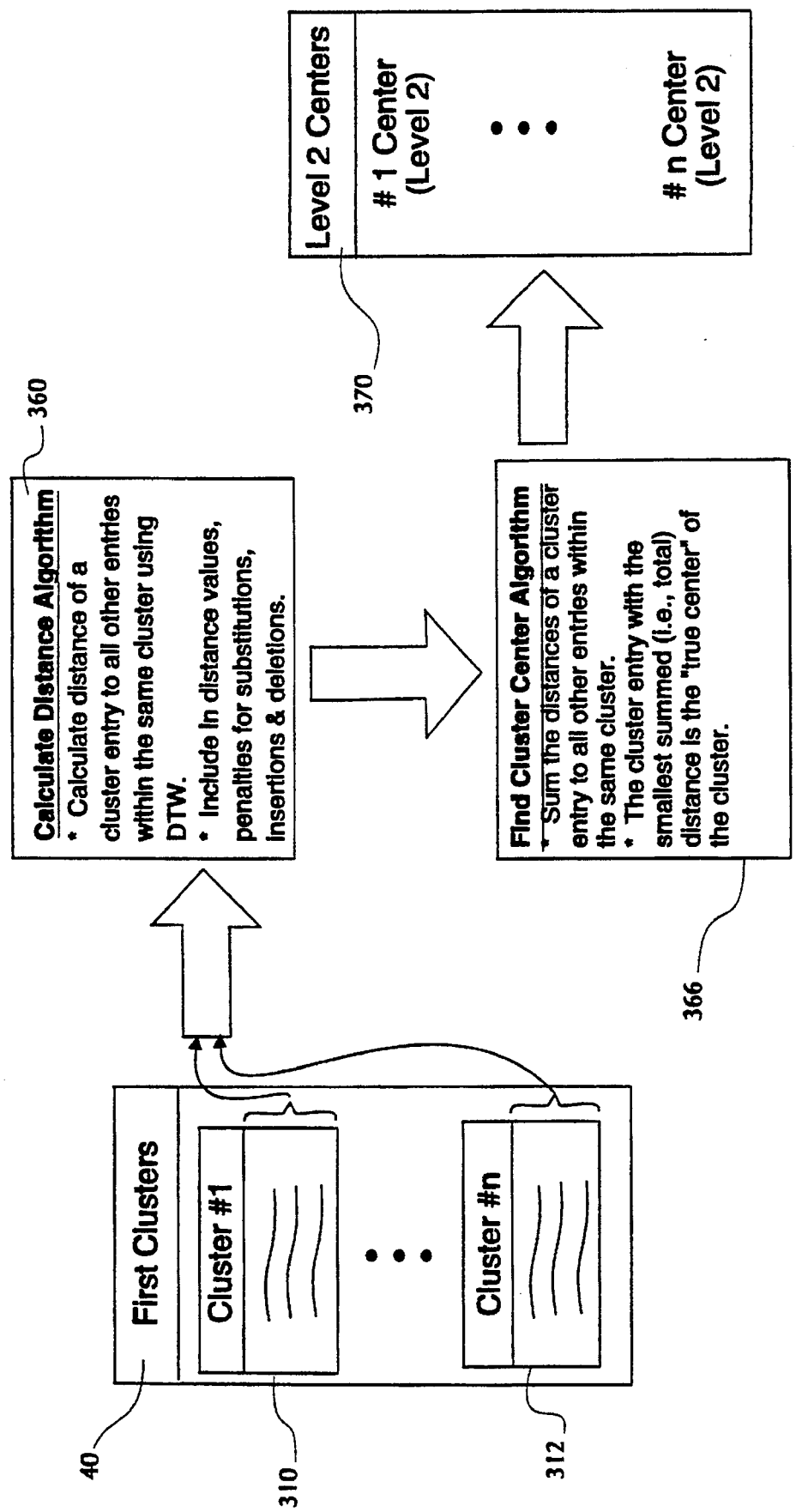
FIG. 8 is a flow diagram that shows the development of the Level 2 cluster centers.

FIG. 8 depicts the steps to extract the Level 2 centers from the first clusters 40. The DTW algorithm is used for each entry within a first cluster to find the distance of that entry to every other entry within that particular cluster. After step 360 calculates the distances, step 366 finds the cluster centers. First, the distances of a cluster entry to all other entries within the same cluster is summed. The cluster entry with the smallest summed (i.e., total) distance, is the "true center" of the cluster. The term "center" is used here in the same manner as the term "center" when referring to a center of a circle, since a center is the place where the distance from all other points is a minimal. The evaluation of each first cluster in accordance with steps 360 and 366 yields the Level 2 cluster centers 370.

For a further understanding see the Appendix listing containing the code used to calculate the distance of one word relative to another. This listing also shows how the distance algorithm uses penalty factors and how to find a cluster center after the distances have been calculated.

Figure 9:
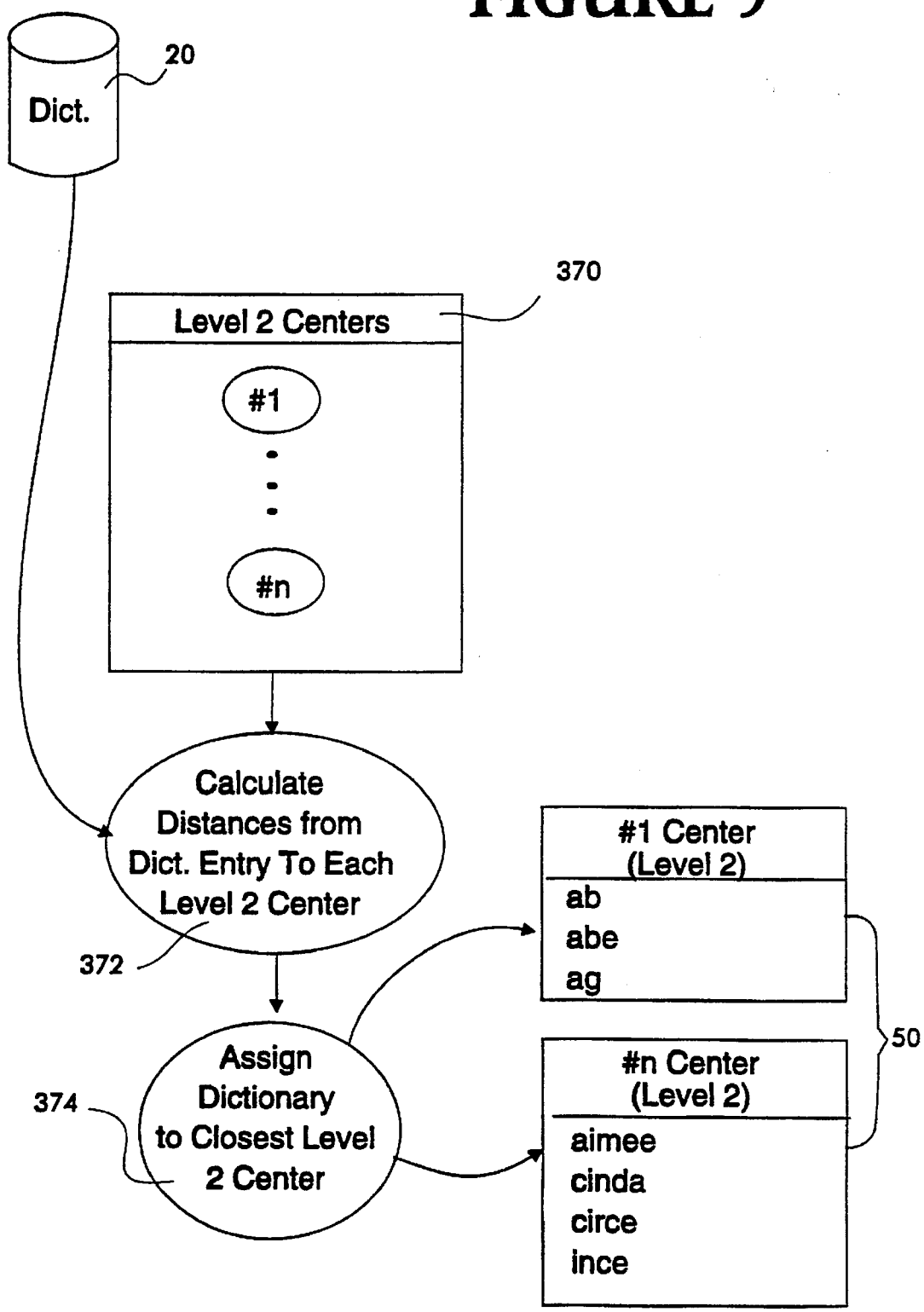
FIG. 9 is the flow diagram that shows the reassigning of the dictionary entries to form second clusters.

FIG. 9 shows the last step in the database clustering system. FIG. 9 depicts the steps to form the second clusters based upon the dictionary 20 and the centers of the first clusters, i.e. the Level 2 centers 370. In a manner similar to the formation of the first clusters, step 372 calculates the distance of each dictionary entry from each Level 2 center using the DTW algorithm. Step 374 then assigns a dictionary entry the Level 2 center representing the closest match. The result of steps 372 and 374 is the second clusters 50.

FIG. 10 shows an example of several second clusters and their associated centers. A comparison of the second clusters (FIG. 10) to the first clusters (FIG. 4) shows that the sizes of the clusters may vary for second clusters as well as the length of the various dictionary entries that are a part of a particular cluster.

The presently preferred embodiment stores the second clusters as the final representation of the dictionary. Typically it will comprise less than 300 clusters, thus effecting a concise representation of the dictionary 20. Using the invention a dictionary whose entries may number as many as 70,000 or greater, can now be more quickly searched by first considering only the centers of a second cluster. Thus, only several hundred comparisons initially need to be done. Once one or several closest centers are located the input word can be quickly matched to a dictionary entry. The present invention yields an order of magnitude reduction in computational processing needed to find dictionary entries that are the closest to the input word. While the invention has been illustrated in an embodiment that stops after created the second clusters, the principles of this technique can be extended, by iteration, to build third clusters, fourth clusters and so forth, if desired. Those skilled in the art can now appreciate from the foregoing description that the broad teachings of the present invention can be implemented in a variety of forms and for a variety of different dictionaries. While the principles are readily adapted to dictionary look-up and speech recognition systems, these principles also work for other types of data, such as data used in pattern recognition. Therefore, while this invention has been described in connection with particular examples thereof, the true scope of the invention should not be so limited since other modifications will become apparent to the skilled practitioner upon a study of the drawings, specification and following claims.

APPENDIX

```c
/***************************************************/*
                          Module "GetDistance.c"
/***************************************************/* include <stdio.h>
include <stdlib.h>
include <string.h> define   MAXLETTERS   26 static int subPEN = 8;
static int delPEN =14;
static int insPEN = 12;
static int lightSubPEN = 3;
static int midSubPEN = 6;

#define   TRUE     1
define   FALSE    0 int trace = FALSE;        /* trace flags defined in HVite */ char **dictionary;              /* array of dictionary words */
int nDictionary;                /* number of words in dictionary */
int *length;                    /* length of each word in dictionary */ typedef struct {
    int score;
  } Cell;

static Cell **grid;    /* matrix of cells */ static int matrix_PEN[MAXLETTERS][MAXLETTERS];
static int offset;

/* GetDistance: get the distance between word test_nLabels and word
    ref_nLabels */
int GetDistance(int test_index, int ref_index, char **cur_dic )
{
  int i, testSize, refSize;
  int column_best_score;
  int h,d,v,j;
  int distance;
  Cell *gridi, *gridi1;
  char *test, *ref;
```

```
int test_nLabels;
int ref_nLabels;

test_nLabels = strlen(cur_dic[test_index ]);
ref_nLabels = strlen(cur_dic[ref_index ]);

test = cur_dic[test_index];
ref = cur_dic[ref_index];

/* CreateGrid: Create a grid of cells of the given dimensions */ testSize = test_nLabels; refSize = ref_nLabels;
if ((grid = (Cell **)malloc((testSize+1)*sizeof(Cell *))) == NULL)
   printf("CreateGrid: Cannot create grid pointer array");
for (i=0; i<=testSize;i++)
   if ((grid[i] = (Cell *) calloc(refSize+1,sizeof(Cell))) == NULL)
      printf("CreateGrid: Cannot create grid column %d",i);
grid[0][0].score = 0;

for (i=1;i<=testSize;i++) {
   grid[i][0] = grid[i-1][0];
   grid[i][0].score=grid[i][0].score + insPEN;
} for (i=1;i<=refSize;i++) {
   grid[0][i] = grid[0][i-1];
   grid[0][i].score=grid[0][i].score + delPEN;
}

/* DoMatch part */ d=h=v=0;
for (i=1;i<=test_nLabels;i++){
   gridi = grid[i]; gridi1 = grid[i-1];
   for (j=1;j<=ref_nLabels;j++) {
      h = gridi1[j].score + insPEN;
      d = gridi1[j-1].score;
      if (ref[j-1] != test[i-1]) {
      d = d + matrix_PEN[(int)(ref[j-1])-offset][(int)(test[i-1])-offset];
      }
      v = gridi[j-1].score + delPEN;
      if (d<=h && d<=v) {       /* hit or substitution */
         gridi[j] = gridi1[j-1];
         gridi[j].score = d;
      } else if (h<v) {         /* insertion */
         gridi[j] = gridi1[j];
         gridi[j].score = h;
      } else {                  /* deletion */
         gridi[j] = gridi[j-1];
         gridi[j].score = v;
      }
   }  /* for j */
```

13

```
    /* find the best score in this column */
    for (j=1;j<=ref_nLabels;j++) {
      if ( gridi[j].score < column_best_score )
      column_best_score = gridi[j].score;
    }
  } /* for i */ distance = grid[test_nLabels][ref_nLabels].score;

/* Free Grid - I heard it that time! */ for (i=0;i<=test_nLabels;i++)
    free(grid[i]);
  free(grid);

return distance;
} void modif_matrix_PEN(tab, nb_tab, penalty)
int tab[];
int nb_tab;
int penalty;
{
  int i,j;
  for(i=0;i<nb_tab;i++)
    for(j=0;j<nb_tab;j++)
      if(tab[i]!=tab[j]) matrix_PEN[tab[i]][tab[j]]=penalty;
}

/* initializes the penalty matrix when the function "MatchHypotheses()"
   is first called                                                    */
void initialize()
{
  int i, j, tab[MAXLETTERS];

/* initialize penalty matrix */ for(i=0;i<MAXLETTERS;i++)
    for(j=0;j<MAXLETTERS;j++)
      matrix_PEN[i][j]=subPEN;

for(i=0;i<MAXLETTERS;i++)
    matrix_PEN[i][i]=0;

offset=(int)'a';

tab[0]='b'-offset;
  tab[1]='c'-offset;
```

```
tab[2]='d'-offset;
tab[3]='e'-offset;
tab[4]='p'-offset;
tab[5]='t'-offset;
tab[6]='v'-offset;
tab[7]='z'-offset;
tab[8]='g'-offset;
modif_matrix_PEN(tab,9,midSubPEN);

tab[0]='a'-offset;
tab[1]='k'-offset;
tab[3]='j'-offset;
modif_matrix_PEN(tab,3,lightSubPEN);

tab[0]='a'-offset;
tab[1]='h'-offset;
modif_matrix_PEN(tab,2,lightSubPEN);

tab[0]='a'-offset;
tab[1]='e'-offset;
modif_matrix_PEN(tab,2,lightSubPEN);

tab[0]='k'-offset;
tab[1]='h'-offset;
modif_matrix_PEN(tab,2,lightSubPEN);

tab[0]='p'-offset;
tab[1]='t'-offset;
modif_matrix_PEN(tab,2,lightSubPEN);

tab[0]='b'-offset;
tab[1]='d'-offset;
tab[2]='t'-offset;
modif_matrix_PEN(tab,3,lightSubPEN);

tab[0]='c'-offset;
tab[1]='t'-offset;
modif_matrix_PEN(tab,2,lightSubPEN);

tab[0]='e'-offset;
tab[1]='t'-offset;
modif_matrix_PEN(tab,2,lightSubPEN);

tab[0]='f'-offset;
tab[1]='s'-offset;
modif_matrix_PEN(tab,2,lightSubPEN);

tab[0]='g'-offset;
tab[1]='t'-offset;
modif_matrix_PEN(tab,2,lightSubPEN);

tab[0]='m'-offset;
```

```
    tab[1]='n'-offset;
    modif_matrix_PEN(tab,2,lightSubPEN);

tab[0]='p'-offset;
    tab[1]='t'-offset;
    modif_matrix_PEN(tab,2,lightSubPEN);

tab[0]='i'-offset;
    tab[1]='r'-offset;
    modif_matrix_PEN(tab,2,lightSubPEN);

tab[0]='y'-offset;
    tab[1]='i'-offset;
    modif_matrix_PEN(tab,2,midSubPEN);

tab[0]='u'-offset;
    tab[1]='q'-offset;
    modif_matrix_PEN(tab,2,lightSubPEN);
} void cluster_init()
{
  int i;

length = (int *)malloc(nDictionary*sizeof(int));
  for (i=0; i<nDictionary; i++)
    {
       length[i] = strlen(dictionary[i]);
    }
  initialize();
}

/*-----------------------------------------------------------------
   FIND_CENTER.C takes a distance matrix of size 'size' and returns the index of
   the word that's closest to all other words - that is, the sum
   of distances to all other words is less than the sum of distances
   between any other word and all other words.
   -----------------------------------------------------------------*/ include<stdio.h> int find_center(int size, int **distance)
   {
   int i, j;          /*** counters            ***/
   int sum[size];     /*** sum of distances    ***/
   int min_sum;
   int which_center;  /* index of center     */ for( i = 0; i < size; i++)
```

```
    {
      sum[i] = 0;
      for( j = 0; j < size; j++)
        sum[i] += distance[i][j];
    } min_sum = 100*size*size;
which_center = -1;

for( i = 0; i < size; i++)
  if( sum[i] < min_sum )
    {
      min_sum = sum[i];
      which_center = i;
    } if( which_center == -1)
  {
    printf("\nforget it.  All these suck");
    printf("\nsize=%d",size);
      printf(" %d",sum[i]);
    for(i=0;i<size;i++)
      {
      for(j=0;j<size;j++)
        printf("%d  ",distance[i][j]);
      printf("\n");
      }
    fflush(stdout);
    exit(0);
  }
return(which_center);
}
```

What is claimed is:

1. A method of constructing optimally clustered dictionary for electronic speech and text recognition, comprising:

provide a dictionary comprising a plurality of dictionary entries;

using a predefined rule-based system to identify from said dictionary a plurality of first cluster centers;

subdividing the dictionary into a plurality of first clusters by comparing each entry of the dictionary to each of the first cluster centers and assigning each of at least a portion of the entries of the dictionary to the one of said first cluster centers that represents the closest degree of similarity;

for each of the first clusters, identifying a cluster center to define a plurality of second cluster centers;

subdividing the dictionary into a plurality of second clusters by comparing each entry of the dictionary to each of the second cluster centers and assigning each entry to said second cluster centers that represent a close degree of similarity.

2. The method of claim 1 wherein said step of using a predefined rule-based system to identify from the dictionary a plurality of first cluster centers, further including the steps of:

sorting said dictionary by length of said dictionary entries to form groups of dictionary entries; and sorting alphabetically said dictionary entries within each said groups of dictionary entries.

3. The method of claim 2 wherein said step of identifying a plurality of first cluster centers, further including the step of:

identifying a first cluster center when a first letter of said alphabetically sorted dictionary entries changes.

4. The method of claim 1 wherein said step of subdividing the dictionary into a plurality of first clusters further including the step of:

comparing each entry of the dictionary to each of the first cluster centers using a dynamic time warping process.

5. The method of claim 1 wherein said step of identifying a cluster center to define a plurality of second cluster centers, further including the steps of:

using a dynamic time warping process applied to each entry assigned to said first center clusters to every other entry assigned to the same said first center clusters;

summing the distances of each entry assigned to said first center clusters to every other entry assigned to the same said first center clusters; and selecting as second cluster centers those entries which have the smallest summed distance within their respective said second clusters.

6. The method of claim 1 wherein said step of subdividing the dictionary into a plurality of second clusters by comparing each entry of the dictionary to each of the second cluster centers and assigning each entry to said second cluster centers that represent a close degree of similarity further including the step of:

comparing each entry of the dictionary to each of the second cluster centers using a dynamic time warping process.

7. An apparatus for constructing optimally clustered dictionary for electronic speech and text recognition, comprising:

a dictionary comprising a plurality of dictionary entries;

a rule-based system including rules to identify from said dictionary a plurality of first cluster centers;

first cluster centers generation means coupled to said dictionary and said rule-based system for generating first cluster centers from said dictionary;

weighting determination means for determining a degree of similarity;

first cluster generation means coupled to said first cluster centers generation means, said weighting determination means, and said dictionary for generating a plurality of first clusters based on the closest degree of similarity between said dictionary entries and said first cluster centers;

second cluster centers generation means coupled to said second cluster generation means and said weighting determination means for generating second cluster centers from said first clusters;

second cluster generation means coupled to said second cluster centers generation means, said weighting determination means, and said dictionary for generating a plurality of second clusters based on the closest degree of similarity between said dictionary entries and said second cluster centers.

* * * * *